United States Patent [19]

Krass

[11] Patent Number: 4,564,385

[45] Date of Patent: Jan. 14, 1986

[54] HERBICIDALLY ACTIVE SUBSTITUTED DIPHENYL ETHER OXIME DERIVATIVES

[75] Inventor: Dennis K. Krass, Canal Fulton, Ohio

[73] Assignee: PPG Industries, Inc., Pittsburgh, Pa.

[21] Appl. No.: 695,500

[22] Filed: Jan. 28, 1985

Related U.S. Application Data

[60] Continuation of Ser. No. 601,460, Apr. 18, 1984, abandoned, which is a continuation-in-part of Ser. No. 373,815, Apr. 30, 1982, which is a division of Ser. No. 136,171, Apr. 15, 1980, Pat. No. 4,344,789, which is a continuation-in-part of Ser. No. 38,043, May 11, 1979, abandoned.

[51] Int. Cl.$^4$ .............................................. A01N 37/42
[52] U.S. Cl. .......................................... 71/98; 71/108; 71/105; 71/115; 562/435; 562/426; 562/440; 560/21; 560/35; 560/15; 260/465 E
[58] Field of Search ..................... 562/435, 440, 426; 560/15, 21, 35; 71/108, 105, 115, 98; 260/465 E

[56] References Cited

U.S. PATENT DOCUMENTS

| | | | |
|---|---|---|---|
| 3,983,168 | 9/1971 | Theissen | 71/111 |
| 4,039,588 | 8/1977 | Wilson et al. | 71/105 |
| 4,060,686 | 11/1977 | Bradshaw et al. | 560/35 |
| 4,063,929 | 12/1977 | Bayer et al. | 71/115 |
| 4,093,446 | 6/1978 | Bayer et al. | 71/109 |
| 4,263,041 | 4/1981 | Grove | 71/98 |
| 4,419,123 | 12/1983 | Swithenbank | 71/98 |
| 4,490,167 | 12/1984 | Pissiotas et al. | 71/105 |

*Primary Examiner*—James H. Reamer
*Attorney, Agent, or Firm*—Edward J. Whitfield

[57] ABSTRACT

This invention relates to certain herbicidally active substituted diphenyl ether oxime derivatives, herbicidal compositions of the same and the use thereof for preemergence and postemergence control of noxious plants, i.e., weeds.

6 Claims, No Drawings

HERBICIDALLY ACTIVE SUBSTITUTED DIPHENYL ETHER OXIME DERIVATIVES

CROSS REFERENCE TO RELATED APPLICATION

This is a continuation of application Ser. No. 601,460, filed Apr. 18, 1984, now abandoned, which is a continuation-in-part of copending application Ser. No. 373,815, filed Apr. 30, 1982, which is a division of application Ser. No. 136,171, filed Apr. 15, 1980, now U.S. Pat. No. 4,344,789, which is a continuation-in-part of application Ser. No. 38,043 filed May 11, 1979, since abandoned.

FIELD OF THE INVENTION

This invention relates to certain substituted diphenyl ether oxime derivatives and to the use of same to control the growth of noxious plants, i.e., weeds.

DESCRIPTION OF THE INVENTION

This invention provides herbicidally active substituted diphenyl ether oxime compounds represented by the Formula I:

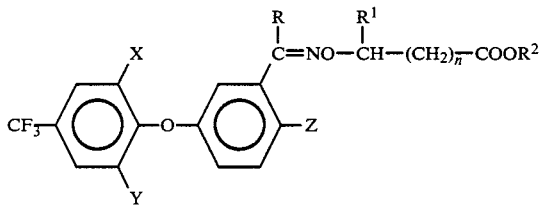

wherein:
X and Y are hydrogen or halogen provided that at least one of X or Y is halogen;
Z is nitro, halogen or cyano;
R is hydrogen, halogen, $C_1$ to $C_4$ alkyl or haloalkyl, $C_1$ to $C_4$ alkoxy or alkylthio, mono or dialkylamino;
$R^1$ is hydrogen or $C_1$ to $C_4$ alkyl;
$R^2$ is hydrogen or $C_1$ to $C_{10}$ alkyl, haloalkyl or alkoxyalkyl; and
n is 0, 1, 2, or 3 with the provisos that when R is hydrogen or alkyl, $R^1$ is hydrogen or methyl, $R^2$ is hydrogen, alkyl or a salt ion, and X and Y are selected from hydrogen or chlorine, then n is 1, 2 or 3.

It is of course understood that agronomically acceptable salts of the Formula I compounds are within the scope of this invention, e.g., compounds wherein $R^2$ is an alkali metal ion, ammonium or substituted ammonium ion.

Suitable alkyl radicals of which the various 'R' groups are representative include methyl, ethyl, n-propyl, iso-propyl, n-butyl, t-butyl or iso-butyl. Chloromethyl, chloroethyl, dichloroethyl, bromomethyl, bromoethyl, trifluoromethyl trifluoroethyl, trichloromethyl and the like are exemplary haloalkyls. As examples of alkoxy and alkylthio radicals there may be mentioned methoxy, ethoxy, propoxy, methylthio, ethylthio or the like. Mono or dialkyl amino groups include methylamino, dimethylamino, methylethylamino, diethylamino or the like. Halogens represented by X, Y, and Z include bromine, chlorine or fluorine. Sodium, potassium or lithium, preferably sodium or potassium, are exemplary of alkali metal ion represented by $R^2$.

Preferred compounds of the Formula I are those wherein X is halogen, e.g., fluorine or bromine; Y is hydrogen; Z is nitro or halogen; R is alkyl or haloalkyl; $R^1$ is hydrogen; $R^2$ is alkyl or haloalkyl; and n is 0.

Compounds of the Formula I may be prepared using techniques known to and starting materials available to the art. For example, a Formula I compound may be prepared by reacting an appropriately substituted diphenyl ether oxime of the Formula II:

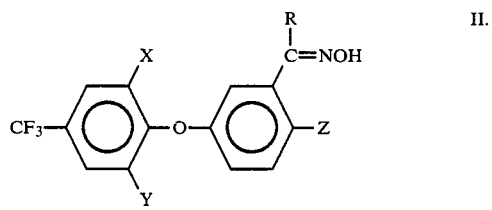

wherein X, Y, Z and R are as previously defined, with an appropriately substituted haloalkanoic acid or ester of the Formula III:

wherein $R^1$, $R^2$ and n are as previously defined and Hal is halogen, e.g., bromine or chlorine.

The following Examples are illustrative of the preparation of certain compound of this invention.

EXAMPLE I

Preparation of:
5-(2-chloro-4-trifluoromethylphenoxy)-2-nitroacetophenone oxime-O-(propionic acid, methyl ester)

A solution of 3.74 grams (0.01 mole) of 5-(2-chloro-4-trifluoromethylphenoxy)-2-nitroacetophenone oxime in 20 milliliters of acetonitrile was treated with 1.82 grams (0.011 mole) of methyl-3-bromopropionate, 0.1 gram (0.0006 mole) of potassium iodide and 1.52 grams (0.011 mole) of anhydrous potassium carbonate. Since there was no apparent reaction after about three days stirring at ambient temperature, the flask was fitted with a reflux condenser and the reaction mixture was refluxed for about 18 hours. The reaction mixture (which had turned dark brown) was cooled and stripped of solvent. The residue was then dissolved in a mixture of methylene chloride and water. The organic phase was washed with water, dried over anhydrous magnesium sulfate and filtered. The filtrate was stripped of solvent affording 4.47 grams of an orange oil. This oil was chromatographed on a silica gel column wet-packed with a 95:5 V/V mixture of benzene:ethyl alcohol, which solvent was also used as the eluent. The appropriate fractions, after being analyzed by TLC, were combined and stripped of solvent affording 2.09 grams of a yellow oil identified by NMR and MS analyses as the desired product.

EXAMPLE II

Preparation of:
5-(2-fluoro-4-trifluoromethylphenoxy)-2-nitroacetophenone oxime-O-(acetic acid, methyl ester)

A mixture of 1.35 grams (0.0075 mole) of 3-fluoro-4-hydroxybenzotrifluoride, 10 milliliters of dimethyl sulfoxide and 1.14 grams (0.00825 mole) of potassium carbonate was treated with 2.02 grams (0.0075 mole) of 5-fluoro-2-nitroacetophenone oxime-O-(acetic acid, methyl ester). The flask was fitted with an air condenser and drying tube and placed in an oil bath maintained at 55° C. After stirring overnight in the oil bath, the reaction mixture was stripped of solvent, leaving a greenish-black residue. Addition of a mixture of methylene chloride and water resulted in disappearance of the dark color and formation of two light orange layers. The organic layer was washed with 2 percent sodium hydroxide solution and saturated sodium chloride solution and dried over anhydrous magnesium sulfate. Filtration and removal of solvent afforded 2.30 grams of an orange oil identified by NMR and MS analyses as the desired product.

EXAMPLE III

Preparation of:
5-(2-chloro-4-trifluoromethylphenoxy)-2-nitroacetophenone oxime-O-(acetic acid, 2,2,2,-trichloroethyl ester)

A solution of 2.75 grams (0.02 mole) of freshly distilled trichloroethanol, 5 milliliters of dry chloroform and 0.41 gram (0.004 mole) of triethylamine was treated with 0.004 mole of 5-(2-chloro-4-trifluoromethylphenoxy)-2-nitroacetophenone oxime-O-acetyl chloride in 8 milliliters of carbon tetrachloride over a fifteen minute period. The resultant clear orange solution was stirred overnight at ambient temperature. The reaction mixture was then stripped of solvent and the residue was dissolved in a mixture of water and and methylene chloride. After phase separation, the organic phase was washed consecutively with 2×75 milliliter portions of 5 percent sodium bicarbonate solution and saturated sodium chloride solution. After drying over anhydrous magnesium sulfate, the reaction was filtered and stripped of solvent affording 2.47 grams of an orange oil identified by NMR and MS analyses as the desired product.

EXAMPLE IV

Preparation of:
5-(2-chloro-4-trifluoromethylphenoxy)-2-nitroacetophenone oxime-O-(acetic acid, 2-chloroethyl ester)

A solution of 0.0075 mole of 5-(2-chloro-4-trifluoromethylphenoxy)-2-nitroacetophenone oxime-O-acetyl chloride dissolved in 30 milliliters of dry carbon tetrachloride was treated with a solution of 3.0 grams (0.015 mole) of 2-chloroethanol and 0.81 grams (0.008 mole) of triethylamine over a 2 to 3 minute period. After stirring overnight at ambient temperature, the reaction mixture was transferred to a separatory funnel, washed consecutively with 2×100 milliliter portions of water and saturated sodium chloride solution. After drying over anhydrous magnesium sulfate, the organic phase was filtered and stripped of solvent affording 3.31 grams of a viscous orange oil. 2.0 grams of this oil were dissolved in 1:2 V/V mixture of ethyl acetate:hexane and added to the top of a column containing 100 grams of silica gel wet-packed with the ethyl acetate:hexane solvent mixture. The column was eluted with the ethyl acetate:hexane solvent mixture. Appropriate fractions, after being combined and stripped of solvent, afforded 1.12 grams of a yellow oil identified by NMR and MS analyses as the desired product.

EXAMPLE V

Preparation of:
5-(2-chloro-4-trifluoromethylphenoxy)-2-nitroacetophenone oxime-O-(acetic acid, 2,2-dichloroethyl ester)

To a solution of 2.87 grams (0.025 mole) of 2,2-dichloroethanol in 5 milliliters of dry carbon tetrachloride was added 10 milliliters of a solution of 0.005 mole of 5-(2-chloro-4-trifluoromethylphenoxy)-2-nitroacetophenone oxime-O-acetyl chloride in dry carbon tetrachloride over a 5 minute period. To the resulting clear, yellow solution was added dropwise with stirring, over a 2 to 3 minute period, 0.51 grams (0.005 mole) of triethylamine. The reaction mixture was stirred at a temperature of 40°–45° C. for about 2 days. The reaction mixture was then stripped of solvent and the residue was triurated with water, dissolved in methylene chloride and washed with water, 5 percent sodium bicarbonate solution and saturated sodium chloride solution. After drying over anhydrous magnesium sulfate, the organic layer was filtered and stripped of solvent affording 2.72 grams of a viscous orange oil. 2.0 grams of this oil were dissolved in 1:2 V/V mixture of ethyl acetate:hexane and added to the top of a column containing 95 grams of silica gel wet-packed with the ethyl acetate:hexane solvent mixture. The column was eluted with a 37:63 V/V mixture of ethyl acetate:hexane. Appropriate fractions, after being combined and stripped of solvent, afforded 0.04 grams of a yellow oil identified by NMR and MS analyses as the desired product.

EXAMPLE VI

Preparation of:
5-(2-chloro-4-trifluoromethylphenoxy)-2-nitroacetophenone oxime-O-(acetic acid, 2,2,2-trifluoroethyl ester)

To a solution of 2.50 grams (0.025 mole) of 2,2,2-trifluoroethanol in 5 milliliters of dry carbon tetrachloride was added 0.005 mole of 5-(2-chloro-4-trifluoromethylphenoxy)-2-nitroacetophenone oxime-O-acetyl chloride dissolved in 10 milliliters of dry carbon tetrachloride. The acid chloride solution was added dropwise, with stirring, over a 5 minute period. To this stirred solution was added, dropwise over a 2–3 minute period, 0.51 gram (0.005 mole) of triethylamine. The flask was fitted with a condenser and drying tube and the reaction mixture was stirred overnight at 40°–45° C. The reaction mixture was then stripped of solvent and the residue was dissolved in methylene chloride and washed with water, 5 percent sodium bicarbonate solution and saturated sodium chloride solution. After drying over anhydrous magnesium sulfate, the organic phase was filtered and stripped of solvent affording 2.49 grams of an orange oil identified by NMR and MS analyses as the desired product.

Although preparation of certain compounds of the invention have been illustrated in some detail by the foregoing Examples, it is to be understood that other compounds of the invention may be readily prepared by those skilled in the art using the same or similar techniques and by varying the choice of starting materials.

Weed control in accordance with this invention is effected by application, either before or after emergence of weeds, of a herbicidally effective amount of a compound of this invention. It is, of course, to be understood that the term "a compound of this invention" also includes mixtures of such compounds.

The term "herbicidally effective amount" is that amount of a compound of this invention required to so injure or damage weeds such that the weeds are incapable of recovering following application. The quantity of a compound of this invention applied in order to exhibit a satisfactory herbicidal effect may vary over a wide range and depends on a variety of factors, such as, for example, hardiness of a particular weed species, extent of weed infestation, climatic conditions, soil conditions, method of application, and the like. Typically, as little as one or less pound per acre of a compound of this invention would be expected to provide satisfactory weed control, although in some instances application rates in excess of one pound per acre; e.g., up to 5 or more pounds per acre might be required. Of course, the efficacy of a particular compound against a particular weed species may readily be determined by routine laboratory or field testing in a manner well known to the art. It is expected that satisfactory weed control can be had at a rate of application in the range of 0.1 to 1.0 pound per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegetative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metolachlor and N,N-dialkyl thiocarbamates such as EPTC, butylate or vernolate. These, as well as other herbicides described, for example, in the *Herbicide Handbook of the Weed Science Society of America*, may be used in combination with a compound or compounds of the invention. Typically such formulations will contain from about 5 to about 95 percent by weight of a compound of this invention.

The herbicidal formulations contemplated herein can be applied by any of several methods known to the art. Generally, the formulation will be surface applied as an aqueous spray. Such application can be carried out by conventional ground equipment, of if desired, the sprays can be aerially applied. Soil incorporation of such surface applied herbicides is accomplished by natural leaching, and is of course facilitated by natural rainfall and melting snow. If desired, however, the herbicides can be incorporated into the soil by conventional tillage means.

The compounds prepared as described in the Examples were individually screened for herbicidal efficacy, against a variety of broadleaf and grassy weed species, under controlled laboratory conditions of light, humidity and temperature. Solvent solutions of said compounds were applied, both preemergence and postemergence, to test flats containing the various weed species, and herbicidal efficacy was determined by periodic visual inspection, after application of the compounds. Herbicidal efficacy was determined on a scale of from 0 (no injury) to 10 (all plants dead).

Basis these screening tests, compounds of this invention are believed effective for preemergence or postemergence control of a wide variety of broadleaf and grassy weeds. Typical of the various species of vegetative growth that may be controlled, combated, or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle, and the like. Also controlled by the compounds of this invention are perennials such as quackgrass, Johnsongrass, Canada thistle, curly dock, field chickweed, dandelion, Russian knapweed aster, horsetail ironweed, sesbania, cattail, wintercress, horsenettle, nutsedge, milkweed, sicklepod, and the like.

Also from the preliminary screening results it is believed that certain of the compounds of the invention, particularly the haloalkyl esters, have improved selectivity and soil persistence. In addition, the invention compounds could be used to effectively control weeds growing amongst crops such as wheat, oats, rice, barley, corn, soybeans, rice, peanuts and the like without causing significant damage to the growing crop.

Although the invention has been described in considerable detail by the foregoing, it is to be understood that many variations may be made therein by those skilled in the art without departing from the spirit and scope thereof, as defined by the appended claims.

I claim:

1. A compound represented by the formula:

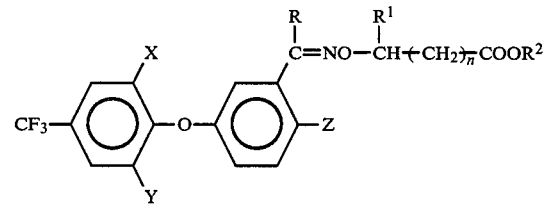

wherein:
X and Y are hydrogen or halogen provided that at least one of X or Y is halogen;
Z is nitro, halogen or cyano;
R is hydrogen, halogen, $C_1$ to $C_4$ alkyl or haloalkyl, $C_1$ to $C_4$ alkoxy or alkylthio, mono or dialkylamino;
$R^1$ is hydrogen or $C_1$ to $C_4$ alkyl;
$R^2$ is hydrogen or $C_1$ to $C_{10}$ alkyl, haloalkyl or alkoxyalkyl; and
n is 0, 1, 2 or 3 with the provisos that when R is hydrogen or alkyl, $R^1$ is hydrogen or methyl, $R^2$ is hydrogen, alkyl or a salt ion and X and Y are selected from hydrogen or chlorine, then n is 1, 2 or 3.

2. A compound of claim 1 wherein X is fluorine or bromine; Y is hydrogen; Z is nitro or halogen; R is alkyl or haloalkyl; $R^1$ is hydrogen; $R^2$ is alkyl or haloalkyl; and n is 0.

3. A compound of claim 1 selected from 5-(2-chloro-trifluoromethylphenoxy)-2-nitroacetophenone oxime-O-(propionic acid, methyl ester), 5-(2-fluoro-4-trifluoromethylphenoxy)-2-nitroacetophenone oxime-O-(acetic acid, methyl ester), 5-(2-chloro-4-trifluoromethylphenoxy)-2-nitroacetophenone oxime-O-(acetic acid, 2,2,2-trichloroethyl ester), 5-(2-chloro-4-trifluoromethylphenoxy)-2-nitroacetophenone oxime-O-(acetic acid, 2-chloroethyl ester), 5-(2-chloro-4-trifluoromethylphenoxy)-2-nitroacetophenone oxime-O-(acetic acid, 2,2-dichloroethyl ester), and 5-(2-chloro-4-trifluoromethylphenoxy)-2-nitroacetophenone oxime-O-(acetic acid, 2,2,2-trifluoroethyl ester).

4. A herbicidal composition containing an inert carrier and a herbicidally effective amount of a compound or mixture of compounds defined in claim 1.

5. In a method of controlling weeds wherein a herbicidally effective amount of herbicide is applied to a growth medium prior to emergence of the weeds therefrom or the weeds subsequent to their emergence from the growth medium, wherein the improvement resides in using as the herbicide a compound or mixture of compounds defined by claim 1.

6. Agronomically acceptable salts of the compounds defined in claim 1.

* * * * *